(12) United States Patent
Holerca et al.

(10) Patent No.: US 8,067,351 B2
(45) Date of Patent: *Nov. 29, 2011

(54) COMPOSITION WITH A COLOR MARKER

(75) Inventors: Marian N. Holerca, Somerset, NJ (US);
Christine Boyke, Somerset, NJ (US);
Mahmoud Hassan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/527,219

(22) PCT Filed: Nov. 11, 2008

(86) PCT No.: PCT/US2008/083086
§ 371 (c)(1),
(2), (4) Date: Aug. 14, 2009

(87) PCT Pub. No.: WO2010/056232
PCT Pub. Date: May 20, 2010

(65) Prior Publication Data
US 2011/0021397 A1 Jan. 27, 2011

(51) Int. Cl.
*C11D 3/40* (2006.01)
(52) U.S. Cl. ....................................................... 510/138
(58) Field of Classification Search .................. 510/138
See application file for complete search history.

(56) References Cited

U.S. PATENT DOCUMENTS

| | | | |
|---|---|---|---|
| 6,147,607 A | 11/2000 | Lynn | |
| 6,211,788 B1 | 4/2001 | Lynn et al. | |
| 6,733,766 B2 | 5/2004 | Gott et al. | |
| 6,814,816 B2 | 11/2004 | Achar et al. | |
| 7,053,029 B2 | 5/2006 | MacDonald et al. | |
| 7,268,104 B2 | 9/2007 | Krzysik et al. | |
| 7,307,051 B2 | 12/2007 | Rich | |
| 2003/0083212 A1* | 5/2003 | Willard et al. | 510/137 |
| 2005/0049157 A1 | 3/2005 | MacDonald et al. | |
| 2005/0231373 A1 | 10/2005 | Lynn et al. | |
| 2006/0004110 A1 | 1/2006 | Sabnis et al. | |
| 2006/0010400 A1 | 1/2006 | Dehlin et al. | |
| 2006/0040835 A1 | 2/2006 | Newkirk et al. | |
| 2006/0135384 A1 | 6/2006 | Luu et al. | |
| 2006/0222601 A1 | 10/2006 | Sabnis et al. | |
| 2006/0222675 A1 | 10/2006 | Sabnis et al. | |
| 2006/0231568 A1 | 10/2006 | Lynn et al. | |
| 2006/0236470 A1 | 10/2006 | Sabnis et al. | |
| 2006/0257439 A1 | 11/2006 | Sabnis et al. | |
| 2006/0287215 A1 | 12/2006 | McDonald et al. | |
| 2007/0142256 A1* | 6/2007 | Lang et al. | 510/141 |
| 2007/0142263 A1 | 6/2007 | Stahl et al. | |
| 2007/0237807 A1 | 10/2007 | Luu et al. | |
| 2008/0081020 A1 | 4/2008 | Huang et al. | |
| 2008/0084315 A1* | 4/2008 | Pittz | 340/573.1 |

FOREIGN PATENT DOCUMENTS

| | | |
|---|---|---|
| JP | 06285140 A | 10/1994 |
| JP | 2002226898 A | 8/2002 |
| WO | 9629047 A1 | 9/1996 |
| WO | 2007068391 A1 | 6/2007 |
| WO | 2008060778 A2 | 5/2008 |

OTHER PUBLICATIONS

SquidSoap, Information on sale in the U.S., circa Jul. 20, 2006.
Dial ColorClean, Information on sale n the U.S., circa Feb. 28, 2008.
Dial ColorClean product available 2008: information from www.dialsoap.com/colorclean.html, image of back of label from Blue Fusion variant, and glycerin analysis.
International Search Report PCT/US2008/083086 mailed Aug. 11, 2009.
U.S. Appl. No. 12/527,225, filed Aug. 14, 2009.
International Search Report from International Application No. PCT/US2008/083087 mailed Aug. 11, 2009.

\* cited by examiner

*Primary Examiner* — John Hardee
(74) *Attorney, Agent, or Firm* — Michael F. Morgan

(57) ABSTRACT

A composition comprising at least one indicator, at least one light stabilizer, and at least one antioxidant. The composition is useful as a cleanser that provides a usage timer based on color change to indicate to a user that sufficient time has elapsed for cleansing.

16 Claims, No Drawings

COMPOSITION WITH A COLOR MARKER

BACKGROUND OF THE INVENTION

"Skin hygiene", particularly of the hands, is a primary mechanism for reducing contact and transmission of infectious agents. According to the Center for Disease Control (CDC), despite the public awareness of the need to wash hands, the recommended methods of washing hands are not followed. The public does not wash frequently enough nor for sufficient time. It should also be noted, however, that too much time washing (scrubbing) could damage the skin. The Association for Professionals in Infections Control and Epidemiology ("APIC") recommends washing hands by wetting hands with running water, applying hand-washing agent, thoroughly distributing it over hands, and vigorously rubbing hands for 10-15 seconds while covering all surfaces of the hands and fingers. The APIC recommends an antimicrobial soap or detergent or alcohol-based rub wash for 10-15 seconds to remove or kill transient micro-organisms, for example, in nursing and food preparation applications. The APIC further recommends an antimicrobial soap or detergent with brushing for at least 120 seconds for surgical applications. It is noteworthy to distinguish the difference between "killing" and "removing" germs. Killing germs can be accomplished by the use of specific ingredients that have deadly effect on the life cycle of the germs. Examples of ingredients that kill germs are Triclosan, PCMX (p-chloro-m-xylenol), Quats, surfactants, etc. An example of a formulation designed to kill germs is a sanitizer gel, which is applied to the hands for the purpose of killing germs, but does not remove the germs. The use of a soap, however, leads to the removal of germs, combined with a mild killing action. In this case, the length of time spent washing the hands can have a great impact on eradication of microbes.

Getting the timing right, however, is an issue. For children it is recommended that they sing the alphabet song once or happy birthday twice in order to wash their hands for 15 seconds. For adults there is no good indicator of when the time is up for efficient hand washing. Thus, there remains a need for a cleaning formulation that will provide an indication to the user how long he has washed his hands to indicate that the cleansing is effective and/or to comply with the health protocols.

SUMMARY OF THE INVENTION

A composition comprising:
a. at least one indicator;
b. at least one light stabilizer; and
c. at least one antioxidant.

The composition can be used in a method comprising
a. applying the composition to a substrate: and
b. leaving the composition on the substrate until a color change is observed.

The present invention provides a color changing composition that remains stable over time on the shelf, but will change color during use.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The composition of the present invention is suitable for providing a color change during use to indicate to a user that sufficient time has passed. The timing can be for many uses, such as to indicate that sufficient cleaning has been done, that the time for application has elapsed, or that the composition is no longer active.

The composition can be used to time the application of a composition. For example, a face mask composition can be applied to deliver an active to skin. The composition can be adjusted to select the time of color change to indicate that sufficient active has been delivered and that the face mask can be removed.

Also, the composition can use color change to indicate that it is no longer active. This would then indicate to a user that the composition can be removed from the substrate on which it was applied.

The timing of the color change can be adjusted to be observable by a user. In certain embodiments, the color change is observed by a user during use before about 5 minutes, about 2 minutes, about 30 seconds, about 25 seconds, about 20 seconds, about 15 seconds, about 10 seconds, about 5 seconds, about 5 to about 30 seconds, or 10 to 30 seconds. The amount of time for color change can be adjusted by changing the concentration of the indicator and/or changing the starting pH. Time is also proportional to the concentration of the indicator. The more indicator that is present, the longer the time. Also, the further the pH is away from skin pH (5.5), the longer the time to color change will be. For example, a composition can be made more basic, which would then take longer to color change as the pH is changed in the system to become more basic.

To provide the color change, an indicator is included. An indicator can be included in any amount to provide the color change to indicate that sufficient time has elapsed for cleaning. As more indicator is included in the composition, the color intensity increases to become more distinctly observable to a user. In one embodiment, the amount of indicator is 0.01 to 10% by weight. In one embodiment, the amount of indicator is 0.01 to 1% by weight. In one embodiment, the amount of indicator is about 0.5% by weight.

Examples of indicators that can be used include, but are not limited to, litmus, carmine, carminic acid, curry powder, thymol blue, pentamethoxy red, tropaeolin O, tropaeolin OO, tropaeolin OOO, 2,4-dinitrophenol, methyl yellow, methyl orange, bromophenol blue, tetrabromophenol blue, alizarin sodium sulfonate, alpha-naphthyl red, para-ethoxychrysoidine, bromocresol green, methyl red, bromocresol purple, chlorophenol red, bromothymol blue, para-nitrophenol, azolitmin, phenol red, neutral red, rosolic acid, cresol red, naphtholphthalein, phenolphthalein, naphtholbenzein, thymolphthalein, nile blue, alizarin yellow, salicyl yellow, diazo violet, nitramine, poirrier's blue, trinitrobenzoic acid, and extracts from beets, blackberries, blueberries, carrots, cherries, delphinium petals, geranium petals, grapes, grape seeds, horse chestnut leaves, morning glories, pansy petals, petunia petals, primrose, poppy petals, purple peonies, red radish, red cabbage, rhubarb, rose petals, strawberries, tea, turmeric, tulip petals, thyme, violet petals, and vanilla. Multiple indicators can be used in combination. In some embodiments, the indicator is selected from litmus and carminic acid. In one embodiment, the indicator is litmus. Litmus can be provided by lichen extract. Litmus changes blue under basic conditions and red under acidic conditions.

The composition can be designed to color change from a first pH to a higher pH or from a first pH to a lower pH. The upper and lower limits for pH are any pH that can be tolerated by skin. In one embodiment, the pH is 2 to 12. The pH of the composition can be adjusted to a desired starting pH by using any desired acid or base. In one embodiment, sodium hydroxide (NaOH) can be selected as the base and citric acid as the acid.

The pH change is provided by the skin during cleansing. The pH of skin is about 5.5. When the composition is basic, the composition becomes more acidic during use. When the composition is acidic, the pH moves to become less acidic.

In one embodiment using litmus as the indicator, the pH can be adjusted to about 9.5 using sodium hydroxide. If the pH is too high, the composition can be adjusted back to about 9.5 using citric acid. As the composition is used, the blue litmus changes to red when contacted with skin.

Indicators may degrade upon exposure to light in solution. For a commercial product that will sit on store shelves and in locations where the product is used, the product will be exposed to light sources. To overcome the exposure to light, a light stabilizer is included to allow the product to remain stable over the targeted life of the product. Additionally, indicators can be oxidized in solution. For a product containing an indicator that contains materials or air that oxidize the indicator, an antioxidant is included to allow the product to remain stable over the targeted life of the product. Light degradation and oxidation is particularly noticeable in litmus and carminic acid.

A light stabilizer is included in the composition. A light stabilizer is any material that stabilizes indicators against degradation from exposure to light. In one embodiment, the light stabilizer is an ascorbate salt. In one embodiment, the light stabilizer is sodium ascorbate. In this embodiment, the sodium ascorbate is particularly useful for litmus and/or carminic acid.

The light stabilizer can be present in any amount that stabilizes the composition. In one embodiment, the amount is 0.01 to 1% by weight. In another embodiment, the amount is 0.05 to 0.5% by weight. In one embodiment, the amount is about 0.25% by weight.

An antioxidant is included in the composition. An antioxidant is any material that stabilizes an indicator against degradation from oxidation. In one embodiment, the light stabilizer is benzophenone-4. In this embodiment, the benzophenone-4 is particularly useful for litmus and/or carminic acid.

The antioxidant can be present in any amount that stabilizes the composition. In one embodiment, the antioxidant is present in an amount of 0.01 to 0.1% by weight. In one embodiment, the amount is about 0.05% by weight.

The light stabilizer and the antioxidant can both independently be selected from the CTFA (Cosmetic, Toiletries, and Fragrance Association) list of antioxidants. See the list that is available circa July 2008 at ctfa-online.org. Examples include, but are not limited to, *Acacia Catechu* Wood Extract, *Acacia Victoriae* Fruit Extract, *Acanthopanax Senticosus* (Eleuthero) Root Water, *Acer Palmatum* Leaf Extract, Acetamidocaproic Acid, Acetyl Benzoyloxy Prasterone, Acetyl Cysteine, Acetyl Hexapeptide-22, 2-Acetylhydroquinone, *Achillea Millefolium* Flower Extract, Adamantanylcarboxamido Hydroxylbenzamide, Adamantanylcarboxamido Methylhydroxylbenzamide, Adamantanyl Dihydrocaffeamide, Adamantanyl Dihydroxybenzamide, Adamantanyl Hydroxybenzamide, Adamantanyl Hydroxylterephthalamide, Adamantanyl Methylhydroxylterephthalamide, Adamantanyl Trihydroxybenzamide, *Aesculus Hippocastanum* (Horse Chestnut) Extract, *Aframomum Angustifolium* Leaf Oil, *Agastache Rugosa* Extract, *Agrimonia Eupatoria* Root Extract, *Ajuga Reptans* Cell Culture Extract, *Ajuga Reptans* Leaf Extract, *Alchemilla Vulgaris* Leaf Extract, *Allium Cepa* (Onion) Root Extract, *Allium Fistulosum* Root Extract, *Allium Odorum* Seed Extract, *Alpinia Uraiensis* Stalk/Leaf Water, *Amaranthus Hypochondriacus* Seed Extract, Aminoethanesulfinic Acid, Aminopropyl Ascorbyl Phosphate, Aminopropyl Methylenedioxyphenyl Phosphate, Aminopropyl Tocopheryl Phosphate, *Angelica Furcijuga* Flower/Leaf/Stem Extract, *Angelica Keiskei* Extract, Angoroside C, Anserine, Apigenin, *Apium Graveolens* (Celery) Seed Extract, *Arabidopsis Thaliana* Extract, Arbutin, Alpha-Arbutin, *Arbutus Unedo* Fruit Extract, *Arctium Lappa* Fruit Extract, Argon, *Artemisia Maritima* Extract, *Asarum Heterotropoides* Extract, *Asarum Heterotropoides* Rhizome Extract, Ascorbic Acid, Ascorbic Acid Polypeptide, Ascorbyl Dipalmitate, Ascorbyl Glucoside, Ascorbyl Linoleate, Ascorbyl Methylsilanol Pectinate, Ascorbyl Palmitate, Ascorbyl Phosphate Succinoyl Pentapeptide-12, Ascorbyl Stearate, Ascorbyl Tetraisopalmitate, Ascorbyl Tocopheryl Maleate, Asiaticoside, *Avena Sativa* (Oat) Kernel Extract, *Bacillus*/Rice Bran Extract/Soybean Extract Ferment Filtrate, *Bambusa Vulgaris* Shoot Extract, Benzoguanamine, *Beta Vulgaris* (Beet) Root Powder, *Betula Ermanii* Stem Extract, BHA, BHT, Bis-demethoxycurcumin, Bis-Hydroxyethyl Tocopherylsuccinoylamido Hydroxypropane, Bis-(Tetramethyl Hydroxypiperidinyl) Sebacate, *Boesenbergia Pandurata* Rhizome Extract, *Borago Officinalis* Extract, *Botrytis* Ferment Extract Filtrate, *Buddleja Axillaris* Leaf Extract, Butylated Xylenol, t-Butylbenzamido Hydroxylbenzamide, t-Butylbenzamido Hydroxylphenylacetamide, t-Butylbenzamido Methylhydroxylbenzamide, t-Butylphenyl Imidazolylphenyl Sulfonamide, 4-Butylresorcinol, Caffeic Acid, Calcium Ascorbate, *Calophyllum Inophyllum* Seed Oil, *Camellia Sinensis* Catechins, *Camellia Sinensis* Leaf Extract, *Camellia Sinensis* Leaf Oil, *Campsis Grandiflora* Flower Extract, *Capparis Moonii* Fruit Extract, *Capsella Bursa-Pastoris* Sprout Water, *Capsicum Annuum* Fruit Extract, Carnosic Acid, Carotenoids, *Carpinus Laxiflora* Stem Extract, *Carpinus Tschonoskii* Stem Extract, *Castanopsis Cuspidata* Stem Extract, *Cayaponia Tayuya* Root Extract, *Celosia Cristata* Extract, *Cercis Chinensis* Flower/Leaf/Stem Extract, *Cereus Grandiflorus* (Cactus) Extract, *Chaenomeles Sinensis* Fruit Extract, Chitosan Ascorbate, Chitosan Glycolate, Chitosan Salicylate, Chlorogenic Acids, *Chrysanthellum Indicum* Flower Water, *Chrysanthemum Boreale* Flower Extract, *Chrysanthemum Indicum* Flower/Leaf/Stem Extract, *Cimicifuga Dahurica* Root Extract, *Cimicifuga Racemosa* Root Extract, *Cinnamomum Zeylanicum* Bark Extract, *Citrus Junos* Seed Extract, *Citrus Medica Vulgaris* Fruit Extract, *Citrus Unshiu* Fruit Powder, Cobalt DNA, *Codonopsis Lanceolata* Extract, *Coffea Arabica* Fruit Extract, Colloidal Platinum, *Commelina Communis* Leaf/Flower/Stem Extract, Copper Adenosine Triphosphate, Copper Pyridoxal 5-Phosphate, *Coptis Chinensis* Root Extract, *Cordyceps Sinensis* Extract, *Cornus Controversa* Leaf Extract, Crotonaldehyde, *Cucumaria Frondosa* Extract, Curcumin, *Cyamopsis Tetragonoloba* (Guar) Symbiosome Extract, *Cyclopia Genistoides* Flower/Leaf/Stem Extract, *Cyclopia Genistoides* Leaf Extract, *Cyclopia Subternata* Flower/Leaf/Stem Extract, *Cycnoches Cooperi* (Orchid) Extract, *Cymbidium Goeringii* Extract, *Cynara Cardunculus* Seed Oil, Cysteine, Cysteine HCl, *Davidsonia Pruriens* Fruit Extract, Decapeptide-6. Decapeptide-7, Decursinol, Decyl Mercaptomethylimidazole, Demethoxycurcumin, Diacetylcurcumin, Diamylhydroquinone, Di-t-Butylhydroquinone, Dicetyl Thiodipropionate, *Dic tyophora Indusiata* (Mushroom) Extract, *Dictyopteris Membranacea* Extract, Dicyclopentadiene/t-Butylcresol Copolymer, Digalloyl Trioleate, Dihydroquercetin, Dihydroxy Methylchromone, Diisooctyl Sebacate, Dilauryl Thiodipropionate, Dimethoxybenzamido Phenylhydroxylacetamide, Dimethoxy Di-p-Cresol, Dimethylmethoxy Chromanol, Dimyristyl Thiodipropionate, Dioleyl Tocopheryl Methylsilanol, *Dioscorea Batatas* Extract, Diosmine, *Diospyros Kaki* Calyx Extract, Diretinyl Ether, Disodium Ascorbyl Sulfate, Disodium Isostearyl Ascorbyl Phosphate, Disodium Rutinyl Disulfate, Disodium Salicylphosphate, Disodium Ubiquinone, Distearyl Thiodipropionate, Ditridecyl Thiodipropionate, Dodecyl Gallate, *Dunaliella Bardawil* Powder, *Echinops Sphaerocephalus* Seed Oil, Ellagic Acid, *Empetrum Nigrum* Flower/Fruit/Leaf Extract, Epigallocatechin Gallate, *Epimedium Sagittatum* Leaf/Stem Extract, Ergothioneine, *Erigeron Canadensis* Flower Extract, *Eriobotrya Japonica* Leaf Protoplasts, *Eriocaulon Buergarianum* Flower/Stem Extract, Erythorbic Acid, Ethylbisiminomethylguaiacol Manganese Chloride, Ethyl Ferulate, Ethylhexyl Ferulate, Ethylhexyl Gallate, *Eucommia Ulmoides* Bark Extract, *Euphorbia Jolkini* Extract, *Euphorbia Supina* Stem Extract, *Excoecaria Bicolor* Leaf Extract, Ferulic Acid, Feruloyl Soy Glycerides, *Foeniculum Vulgare* (Fennel) Seed Extract, *Forsythia Suspensa* Fruit Extract, *Fragaria Ananassa* (Strawberry) Seed Oil, *Fragaria Vesca* (Strawberry) Flower Extract, *Fragilaria Pinnata* Extract, Furfuryl Palmitate, Galla Rhois Gallnut Extract, *Ganoderma Japonicum* Mycelium Ferment Extract Filtrate, Genistein Glucoside, Ginkgo Leaf Terpenoids, Glucosylrutin, Glyceryl Chromonyl Ether, Glyceryl Diferulate, *Glycine Max* (Soybean) Symbiosome Extract, *Glycine Soja* (Soybean) Oil, *Glycyrrhiza Glabra* (Licorice) Root Extract, *Glycyrrhiza Glabra* (Licorice) Root Water, *Grifola Frondosa* Fruiting Body Extract, *Grifola Frondosa* (Maitake) Mycelium Ferment Filtrate Extract, *Gynostemma Pentaphyllum* Extract, *Gynostemma Pentaphyllum* Leaf Extract, *Gynostemma Pentaphyllum* Leaf/Stem Extract, *Haematococcus Pluvialis* Extract, *Haematococcus Pluvialis* Oil, *Haematococcus Pluvialis* Powder *Hedera Helix* (Ivy) Extract, Hesperetin, Hesperetin Laurate, Hesperidin Methyl Chalcone, Hexyloxy Trimethylphenol, Honokiol, Human Oligopeptide-9 Hexapeptide-25, Hydrolyzed *Anona Chemmolia* Fruit Extract, Hydrolyzed *Aspergillus*/Ginseng Extract Ferment, Hydrolyzed *Gardenia Florida* Extract, Hydrolyzed Grape Skin, Hydrolyzed *Lycium Barbarum* Fruit Extract, Hydrolyzed Olive Fruit, Hydrolyzed Olive Fruit Extract, Hydrolyzed Proanthocyanidin, Hydrolyzed Rice Leaf Extract, Hydrolyzed *Saccharomyces*/Sodium Selenate Ferment Extract, Hydrolyzed *Sophora Japonica* Fruit Extract, Hydrolyzed Soy Extract, Hydrolyzed *Typha Angustifolia* Pollen/Root Extract, Hydrolyzed Wheat Bran, Hydroquinone, p-Hydroxyanisole, Hydroxydecyl Ubiquinone, Hydroxylamine HCl, Hydroxylamine Sulfate, Hydroxyphenyl Dihydroxybenzamide, *Illicium Religiosum* Branch/Leaf Extract, Inositol Hexaniacinate Hexaascorbate, *Ipomoea Batatas* Tuber Extract, Isooctyl Caprylate/Caprate, Isooctyl Thioglycolate, Isoquercitrin, *Juglans Regia* (Walnut) Seedcoat Extract, *Juniperus Communis* Sprout Extract, Kaempferol, Kojic Acid, Kojyl Glucoside, Kojyl Methylenedioxycinnamate, Kou-Cha Ekisu, *Lactobacillus/Portulaca Oleracea* Ferment Extract, *Lactobacillus*/Rice Bran/*Saccharomyces/Camellia Sinensis* Leaf Extract Ferment, *Lactobacillus/Saccharomyces/Pichia Anomala/Camellia Sinensis* Leaf Extract/*Artemisia Princeps* Leaf Extract/Honey Ferment Filtrate, *Lactobacillus/Saccharomyces/Pichia Anomala/Camellia Sinensis* Leaf Extract/Honey Ferment Extract Filtrate, *Lactobacillus/Saccharomyces/Pichia Anomala/Camellia Sinensis* Leaf Extract/Honey Ferment Filtrate, *Lactobacillus/Wasabia Japonica* Root Ferment Extract, *Larix Sibirica* Wood Extract, *Lawsonia Inermis* (Henna) Extract, *Lens Culinaris* (Lentil) Symbiosome Extract, *Lespedeza Cuneata* Extract, *Ligusticum Striatum* Root Extract, *Lilium Candidum* Flower Extract, *Lindera Strychnifolia* Leaf Extract, Linoleyl Gallate, Linseed Oil Ascorbate Esters, *Liriodendron Tulipifera* Leaf Water, *Lotus Japonicus* Symbiosome Extract, *Lupinus Subcarnosus* Symbiosome Extract, *Lycium Chinense* Fruit Extract, Lycopene, *Maackia Fauriei* Stem Extract, Madecassoside, Magnesium Ascorbate, Magnesium Ascorbate/PCA, Magnesium Ascorbylborate, Magnesium Ascorbyl Phosphate, Magnolia Grandiflora Bark Extract, Magnolol, Malachite Extract, *Mallotus Japonicus* Leaf Extract, Malpighia Punicifolia (Acerola) Fruit Extract, *Malus Domestica* Fruit Extract, Manganese Adenosine Triphosphate, Manganese Dioxide, Manganese Fructose Diphosphate, Manganese Pyridoxal 5-Phosphate, Matrine, *Matteuccia Struthiopteris* Extract, *Medicago Sativa* (Alfalfa) Symbiosome Extract, *Melaleuca Alternifolia* (Tea Tree) Leaf Oil, Melatonin, *Melia Azadirachta* Conditioned Media/Culture, Methoxy PEG-7 Ascorbic Acid, Methoxy-PEG-7 Rutinyl Succinate, Methoxytrimethylphenyl Dihydroxyphenyl Propanol, Methyl Di-t-butyl Hydroxyhydrocinnamate, Methylene Di-t-Butylcresol, 3,4-Methylenedioxybenzyl Methylsulfone, Methyl Methacrylate/Trimethoxysilylpropyl Methacrylate Crosspolymer, Methyl Myristic Acid, Methylsilanol Ascorbate, *Mirabilis Jalapa* Flower Extract, *Momordica Grosvenori* Fruit Extract, *Monascus*/Rice Ferment, *Morus Alba* Fruit Extract, *Morus Alba* Leaf Extract, *Morus Alba* Root Extract, *Morus Bombycis* Extract, *Morus Bombycis* Stem Extract, *Morus Bombycis* Wood Extract, *Murdannia Keisak* Extract, *Murraya Exotica* Leaf Extract, *Musa Balbisiana* Fruit Extract, *Narcissus Tazetta* Bulb Extract, *Nelumbo Nucifera* Seed Extract, Niacinamide Hydroxybenzoate, Nictoflorin, Nordihydroguaiaretic Acid, Octadecyl Di-t-butyl-4-hydroxyhydrocinnamate, Octanicotinoyl Epigallocatechin Gallate, Octapeptide-4, *Olea Europaea* (Olive) Bud Extract, *Olea Europaea* (Olive) Flower Water, *Olea Europaea* (Olive) Fruit Unsaponifiables, Oligopeptide-28, Oligopeptide-29, Oligopeptide-30, Oligopeptide-31, *Orostachys Japonica* Extract, *Oryza Sativa* (Rice) Seed Water, *Oxycoccus Palustris* Seed Oil, *Paecilomyces Japonica*/Grape/Cucumber Juice Extract Ferment Filtrate, Paeonol, Palmatine, Palmitoyl *Camellia Sinensis* Extract, Palmitoyl Coffee Bean Extract, Palmitoyl Grape Seed Extract, Palmitoyl Grapevine Shoot Extract, Palmitoyl Olive Leaf Extract, Pearl Extract, PEG/PPG-2/5 Tocopheryl Ether, PEG/PPG-5/10 Tocopheryl Ether, PEG/PPG-5/20 Tocopheryl Ether, PEG/PPG-5/30 Tocopheryl Ether, PEG/PPG-30/10 Tocopheryl Ether, PEG/PPG-50/20 Tocopheryl Ether, PEG/PPG-70/30 Tocopheryl Ether, PEG/PPG-100/70 Tocopheryl Ether, *Pelvetia Siliquosa* Extract, Pentaerythrityl Tetra-di-t-butyl Hydroxyhydrocinnamate, *Perilla Ocymoides* Seed Extract, Perillyl Alcohol, *Peucedanum Japonicum* Branch Extract, *Phaseolus Angularis* Seed Extract, *Phaseolus Vulgaris* (Kidney Bean) Sprout Extract, *Phellinus Linteus* Extract, Phenethyl Caffeate, Phenylethyl Resorcinol, Phenylthioglycolic Acid, Phloretin, Phloroglucinol, *Physocarpus Amurensis* Stem Extract, Phytosteryl Linoleate, Phytosteryl Linoleate/Linolenate, Piceatannol, *Pikea Robusta* Extract, *Pimpinella Brachycarpa* Extract, *Pinus Densiflora* Extract, *Pinus Densiflora* Leaf Extract, *Pinus Nigra* Bud/Needle Extract, *Pinus Pinaster* Bark/Bud Extract, *Pinus Radiata* Bark Extract, *Pinus Sylves-* tris Bud Extract, Piperlonguminine, *Piper Nigrum* (Pepper) Seed, *Piper Umbellatum* Root Extract, *Pisum Sativum* Symbiosome Extract, *Platycarya Strobilacea* Branch Extract, *Platycodon Grandiflorum* Root Extract, *Pogostemon Cablin* Leaf/Stem Extract, *Polygonum Cuspidatum* Root Extract, Polyquaternium-82, *Porphyridium* Polysaccharide, *Porphyridium* Polysaccharide Hydroxypropyltrimonium Chloride, *Portulaca Oleracea* Flower/Leaf/Stem Extract, Potassium Ascorbyl Tocopheryl Phosphate, Potassium Sulfite, *Pothomorphe Umbellata* Leaf Extract, PPG-2 Tocophereth-5, PPG-5 Tocophereth-2, PPG-10 Tocophereth-30, PPG-20 Tocophereth-50, PPG-30 Tocophereth-70, PPG-70 Tocophereth-100, PPG-5 Tocopheryl Ether, Propyl Gallate, Protocatechuicaldehyde, *Prunella Vulgaris* Extract, *Prunus Cerasus* (Bitter Cherry) Extract, *Prunus Cerasus* (Bitter Cherry) Fruit Extract, *Prunus Cerasus* (Bitter Cherry) Leaf Extract, *Prunus Mume* Flower, *Prunus Mume* Flower Extract, *Prunus Mume* Flower Powder, *Prunus Salicina* Fruit Extract, *Prunus Spinosa* Wood Extract, *Prunus Tomentosa* Fruit Extract, *Pueraria Lobata* Symbiosome Extract, Puerarin, *Punica Granatum* Bark/Fruit Extract, Pyridoxine Hydroxybenzoate, Pyridoxine Hydroxycitrate, Pyridoxine Salicylate, Pyridoxine Serinate, Pyridyloxide t-Butylnitrone, *Pyrus Malus* (Apple) Peel Extract, Quercetin, Quercetin Caprylate, *Quercus Infectoria* Fruit Extract, *Quercus Salicina* Stem Extract, Resacetophenone, Resorcinol, Resveratrol, Retinyl Formyl Aspartamate, Rhodochrosite Extract, *Rhododendron Mucronulatum* Flower Extract, *Rhodymenia Palmata* Extract, *Rhus Javanica* Extract, *Rhus Semialata* Leaf Extract, *Rosa Davurica* Bud Extract, *Rosa Indica* Flower Extract, *Rosa Wichuraiana* Stem Extract, Rosmarinic Acid, *Rosmarinus Officinalis* (Rosemary) Flower Extract, *Rosmarinus Officinalis* (Rosemary) Leaf Extract, *Rubus Arcticus* Fruit Extract, *Rubus Chamaemorus* Fruit Extract, Rutin, Rutinyl Succinate, Ryoku-Cha Ekisu, *Saccharomyces*/Carrageenan Extract/*Sarcodiotheca Gaudichaudii* Extract Ferment, *Saccharomyces/Pueraria Lobata* Symbiosome Extract Ferment, *Saccharomyces/Rhodobacter/Lactobacillus/Leuconostoc/ Streptomyces Griseus/Aspergillus/Bacillus* Ferment Filtrate, Salnacedin, *Sambucus Nigra* Bud Extract, *Sanguisorba Minor* Extract, *Santalum Acuminatum* Fruit Extract, *Sarcodiotheca Gaudichaudii* Extract, *Sargassum Pallidum* Extract, *Sarothamnus Scoparius* Extract, *Sasa Senanensis* Leaf Extract, *Saururus Chinensis* Flower Extract, *Saururus Chinensis* Leaf/Root Extract, *Schinopsis Quebracho-Colorado* Wood Extract, *Schizandra Sphenanthera* Fruit Extract, *Sedum Rosea* Root Extract, Selenium/*Glycine Soja* (Soybean) Sprout Extract, *Sideritis Syriaca* Extract, *Smilax China* Extract, *Smilax China* Fruit Extract, *Smilax China* Root Extract, Smithsonite Extract, Sodium Ascorbate, Sodium Ascorbyl/Cholesteryl Phosphate, Sodium Ascorbyl Phosphate, Sodium Bisulfite, Sodium Erythorbate, Sodium Grape Seed Extract Phosphate, Sodium Metabisulfite, Sodium Phosphono-Pyridoxylidenerhodanine, Sodium Sulfite, Sodium Thioglycolate, Sodium Tocopheryl Phosphate, Sodium Zinc Histidine Dithiooctanamide, *Solanum Lycopersicum* (Tomato) Fruit Extract, *Sophora Flavescens* Root Extract, Sorbityl Furfural, *Spirulina Maxima* Powder, Sponge Extract, Stearyl Gallate, *Stephanandra Incisa* Stem Extract, *Streptococcus Thermophilus/Lactobacillus/Bifidobacterium*/Licorice Root Extract Ferment Filtrate, Succinoyl Ascorbate Pentapeptide-6, *Syzygium Leuhmanii* Fruit Extract, Tangeritin, TBHQ, *Terminalia Ferdinandiana* Fruit Extract, Tetrabutyl Ethylidenebisphenol, Tetrahexyldecyl Ascorbate, Tetrahydrobisdemethoxydiferuloylmethane, Tetrahydrocurcumin Diacetate, Tetrahydrodemethoxydiferuloylmethane, Tetrahydrodiferuloylmethane, Tetramethylbutyl Dihydroxybenzamide, Tetramethylchromanol Glucoside, Teupolioside, *Theobroma Cacao* (Cocoa) Husk Extract, *Theobroma Cacao* (Cocoa) Seed Extract, Thioctic Acid, Thiodiglycol, Thiodiglycolamide, Thiodiglycolic Acid, Thioglycolic Acid, Thiolactic Acid, Thiosalicylic Acid, Thiotaurine, *Thuja Orientalis* Extract, *Thuja Orientalis* Leaf Extract, Thymol Trimethoxycinnamate, Tococysteamide, Tocophereth-5, Tocophereth-10, Tocophereth-12, Tocophereth-18, Tocophereth-50, Tocopherol, Tocophersolan, Tocopheryl Acetate, Tocopheryl Dimethylglycinate, Tocopheryl Dimethylglycinate HCl, Tocopheryl Linoleate, Tocopheryl Linoleate/Oleate, Tocopheryl Nicotinate, Tocopheryl Retinoate, Tocopheryl Succinate, Tocoquinone, Toluene, o-Tolyl Biguanide, *Torilis Japonica* Extract, Totarol, *Trapa Bicornis* Nut Extract, *Tremella Fuciformis* Sporocarp Extract, *Tricholoma Magnivelare* Extract, *Trifolium Pratense* (Clover) Seed Extract, *Trifolium Pratense* (Clover) Symbiosome Extract, *Trigonella Foenum* Symbiosome Extract, Tripropylene Glycol, Tris-BHT Mesitylene, Tris(Nonylphenyl)Phosphite, Trisodium Ascorbyl Isopalmitate Phosphate, Trisodium Ascorbyl Palmitate Phosphate, Trisodium Fructose Diphosphate, Trisodium Resveratrol Triphosphate, *Triticum Aestivum* (Wheat) Leaf Extract, Tyrosyl Histidine HCl, Ubiquinol, Ubiquinone, *Ulva Lactuca* Powder, Uuron-Cha Ekisu, *Vaccinium Macrocarpon* (Cranberry) Fruit Powder, *Vaccinium Myrtillus* Bud Extract, *Vaccinium Myrtillus* Stem Extract, *Vaccinium Vitis-Idaea* Fruit Extract, *Vaccinium Vitis-Idaea* Leaf Protoplasts, *Vaccinium Vitis-Idaea* Seed Oil, *Vanda Coerulea* Extract, *Viburnum Awabuki* Leaf Extract, *Vicia Sativa* Symbiosome Extract, *Viola Mandshurica* Flower Extract, *Vitis Vinifera* (Grape) Fruit Powder, *Vitis Vinifera* (Grape) Juice, *Vitis Vinifera* (Grape) Juice Extract, *Vitis Vinifera* (Grape) Seed Extract, *Vitis Vinifera* (Grape) Skin Extract, *Vitis Vinifera* (Grape) Skin Powder, Volcanic Rock, Wine Extract, Xylyl Dibutylbenzofuranone, Zinc Adenosine Triphosphate, Zinc Ascorbate, Zinc Dibutyldithiocarbamate, Zinc Fructose Diphosphate, and Zinc Pyridoxal 5-Phosphate. In one embodiment, the light stabilizer and the antioxidant are different materials.

In one embodiment, a combination of sodium ascorbate and benzophenone-4 are selected as the light stabilizer and antioxidant, respectively. This combination provides stability to light and oxidation. In one embodiment, the amount of sodium ascorbate is about 0.25% by weight, and the amount of benzophenone-4 is about 0.05% by weight.

Stability is measured up to 13 weeks for compositions placed in sunlight for light stability and for oxidation at 25° C. and 49° C. Light stability is measured by color fading using UV-Vis spectroscopy. Oxidation is measured by color fading using UV-Vis spectroscopy and with pH measurements. This test can be conducted by taking 1 g of sample and diluting with 9 g of water to make a dilute solution. The dilute solution is placed into a UV-Vis spectrometer. The UV-Vis spectrometer settings are: wavelength set to scan 400 nm to 800 nm, scan speed is set to fast, cycle time is 60 seconds, and results are recorded in absorbance units with a lower limit of 0 and an upper limit of 2.

In one embodiment, the composition has a second light absorption value after 13 weeks at 49° C. that is no more than 20% different from a first light absorption value that is measured initially according to a UV-Vis spectrometer test. The wavelength that is selected for the measurement is based on the peak absorption for the indicator that is used. For litmus, the absorption is measured at about 590 nm. When there is more than one indicator used, the absorption measurements are taken at each of the peak absorptions for each material. In other embodiments, the value is not more than 15%, 10%, or 5% different. In one embodiment, the wavelength used for measuring is 590 nm. In one embodiment, the pH does not change more than +/−0.5 units.

When the composition is a cleanser, the composition contains at least one surfactant. The surfactant may be one or more anionic surfactants, amphoteric surfactants, nonionic surfactants, cationic surfactants, and combinations thereof. Those of ordinary skill in the art will be aware of suitable surfactants and other additives readily identifiable from the *International Cosmetic Ingredient Dictionary and Handbook*, 10$^{th}$ ed. (2004). Surfactants can be included in any desired amount. In one embodiment, surfactants are present in the composition in an amount of 0 to 40% by weight. In one embodiment, the surfactants are present in an amount of 1 to 40% by weight. In one embodiment, surfactants are present in the composition in an amount of 5 to 40% by weight. In one embodiment, the surfactants are present in an amount of 1 to 10% by weight.

A variety of anionic surfactants can be utilized in the moisturizing body wash composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used. In one embodiment, the anionic surfactant comprises sodium laureth sulfate, sodium pareth sulfate, and combinations thereof. Anionic surfactants can be included in any desired amount. In one embodiment, anionic surfactants are present in the composition in an amount of 0 to 15% by weight. In one embodiment, anionic surfactants are present in an amount of 4 to 12% by weight.

Amphoteric surfactants may also be included in the composition. These surfactants are typically characterized by a combination of high surfactant activity, lather forming and mildness. Amphoteric surfactants include, but are not limited to, derivatives of aliphatic secondary and tertiary amines in which the aliphatic radical can be straight chain or branched and wherein one of the aliphatic substituents contains 8 to 18 carbon atoms and one contains an anionic water solubilizing group, e.g. carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to a range of betaines including, for example, high alkyl betaines, such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines. Amphoteric surfactants can be included in any desired amount. In one embodiment, amphoteric surfactants are present in the composition in an amount of 0 to 15% by weight. In one embodiment, the amphoteric surfactants are present in the composition in an amount of 1 to 6% by weight.

Examples of nonionic surfactants include, but are not limited to, polysorbate 20, long chain alkyl glucosides having $C_8$-$C_{22}$ alkyl groups; coconut fatty acid monoethanolamides such as cocamide MEA: coconut fatty acid diethanolamides, fatty alcohol ethoxylates (alkylpolyethylene glycols): alkylphenol polyethylene glycols: alkyl mercaptan polyethylene glycols: fatty amine ethoxylates (alkylaminopolyethylene glycols): fatty acid ethoxylates (acylpolyethylene glycols); polypropylene glycol ethoxylates (for example the PLURONIC™ block copolymers commercially available from BASF): fatty acid alkylolamides, (fatty acid amide polyethylene glycols); N-alkyl-, N-alkoxypolyhydroxy fatty acid amides: sucrose esters: sorbitol esters; polyglycol ethers; and combinations thereof. Nonionic surfactants can be included in any desired amount. In one embodiment, nonionic surfactants are present in the composition in an amount of 0 to 3% by weight. In one embodiment, nonionic surfactants are present in the composition in an amount of 0.5 to 1.5% by weight.

Cationic surfactants can also be included in the composition. Examples of cationic surfactants include, but are not limited to any quaternium or polyquaternium compound. Cationic surfactants can be included at any desired level. In one embodiment, cationic surfactants are present in the composition in an amount of 0 to 2% by weight. In one embodiment, cationic surfactants are present in the composition in an amount of 0.1 to 0.3% by weight.

Many additional surfactants are described in McCutcheon's Detergents and Emulsifiers (1989) and other reference materials that are well known to those of ordinary skill in the art.

In one embodiment, the surfactant is a combination of an anionic surfactant and an amphoteric surfactant. In one embodiment, the surfactant comprises a C10-C16 alcohol ethoxylate and cocoamidopropyl betaine. In one embodiment, the alcohol ethoxylate is sodium C10-C16 alcohol ethoxylate.

When the composition is a sanitizer, the composition can contain an alcohol, such as ethanol. Sanitizers can be thickened with any material to provide a desired viscosity to the sanitizer composition. Examples of thickening agents include, but are not limited to, synthetic thickening agents, polymeric gums, polysaccharides, pectin, alginate, arabinogalactan, carrageen, gellan gum, xanthum gum, guar gum, rhamsan gum, furcellaran gum, and other natural gum. A synthetic thickening agent in one embodiment is a polyacrylate. One acrylate aqueous solution s is manufactured by Lubrizol as CARBOPOL™ resins, also known as CARBOMER™, which are hydrophilic high molecular weight, crosslinked acrylic acid polymers. In one embodiment, the polymer is CARBOPOL™ Aqua SF-1. Other polymers that can be used include, but are not limited to, CARBOPOL™ Aqua 30. CARBOPOL™ 940 with a molecular weight of approximately 4,000,000, and CARBOPOL™ 934 with a molecular weight of approximately 3,000,000. The thickening agents can be used alone or in combination. The amount of thickening agent can be any amount that provides for a desired level of thickening. In one embodiment, the thickening agent is present in an amount of 0.01 to 15% by weight of the composition. In other embodiments, the amount of thickening agent is 1% to 10%.

The composition can also contain glycerin. The glycerin can be included in any desired amount. In one embodiment, the amount of glycerin is up to 5% by weight. Glycerin can change the feel of skin after washing. At higher pH, skin can feel tight after washing.

In other embodiments, the composition can contain particulate materials. An example of a particulate material is shea butter beads, such as Butyrospermum Parkii beads from ISP Corp. available as CAPTIVATES™ 2485.

The composition can additionally contain a colorant to adjust the color of the composition to any desired color. The colorant can work in combination with the indicator to provide color to the composition. Even with the colorant present, the indicator still works to change the color of the composition when the pH changes.

Examples of colorants include, but are not limited to, annatto, caramel, carmine, β-carotene, bismuth citrate, disodium EDTA-copper, potassium sodium copper chlorophyllin (chlorophyllin copper-complex), dihydroxyacetone, bismuth oxychloride, guaiazulene, henna, iron oxides, ferric ammonium ferrocyanide, ferric ferrocyanide, chromium hydroxide green, chromium oxide greens, guanine, lead acetate, pyrophyllite, mica, silver, titanium dioxide, aluminum powder, bronze powder, copper powder, ultramarines, manganese violet, zinc oxide, luminescent zinc sulfide, D&C Black No. 2, D&C Black No. 3, FD&C Blue No. 1, D&C Blue No. 4, D&C Brown No. 1 FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2. FD&C Yellow No. 5, FD&C Yellow No. 6, D&C Yellow No. 7, Ext. D&C Yellow No. 7, D&C Yellow No. 8, D&C Yellow No. 10, and D&C Yellow No. 11. In one embodiment, FD&C Blue #1 is used as a second colorant in compositions containing litmus or carminic acid as the indicator. In this embodiment, the Blue #1 is present at 0.003 weight %.

The composition can be formulated to have any desired viscosity. In some embodiments, the composition has Brookfield viscosity of greater than 0 to 35,000 mPas (cps). In one embodiment, the viscosity is less than about 14,000 mPas (cps) so that it is pumpable. In other embodiments, the viscosity is greater than 2500 to 14,000 mPas (cps). Brookfield viscosity is measured on a DVII viscometer with spindle 5 at 20 rpm for 1 minute.

In some embodiments, the composition is formulated as a foaming hand cleanser that has a low viscosity. The viscosity range for foaming liquid hand soap is about 25±15 mPas (cps). Brookfield viscosity is measured on a DVII viscometer with spindle 3 at 100 rpm for 1 minute.

The composition can also be used in a method comprising:
a) applying the composition to a substrate; and
b) leaving the composition on the substrate until a color change is observed.

The color change can be used to indicate that sufficient time has passed for the composition to be effective for its purpose (such as cleansing or sanitizing) or that the composition is no longer active.

In one embodiment, the method comprises:
a) applying the composition to hands;
b) rubbing the hands together until a color change is observed; and
c) rinsing the hands with water.

The color indicator of the composition of this invention is suitable for addition to materials such as toiletries including but are not limited to cleansers, body washes, shower gels, liquid hand soaps, bar soaps, shampoos, conditioners, and sanitizers. The present invention may be used in a number of settings including, but not limited to, private homes, hospitals, work places, childcare centers, nursing homes, schools, restaurants, airports, and food-preparation and food-processing establishments and the like.

SPECIFIC EMBODIMENTS OF THE INVENTION

The invention is further described in the following examples. The examples are merely illustrative and do not in any way limit the scope of the invention as described and claimed. In the examples, the amounts of material are based on the as supplied weight.

Example 1

A liquid hand soap is prepared by mixing of the following ingredients. The amounts listed below are based on the as supplied amount. The pH of the composition is adjusted to about 9.5 using sodium hydroxide. The 0.5 weight % litmus provides about 15 to 20 seconds of time for color change when used with washing hands.

| Material | Amount (weight %) |
|---|---|
| DI Water | Q.S. (about 58) |
| Anhydrous Sodium Sulfate | 0.09 |
| DMDM Hydantoin | 0.4 |
| sodium C10-C16 alcohol ethoxylate (Stepan Steol CS-230) (27.5%) | 29.9 |
| Cocamidopropyl Betaine | 6 |
| Ethylene diamine tetraacetate (39% solution) | 0.26 |
| PEG-120 premix (6.9% PEG-120 methyl glucose dioleate, 1% DMDM Hydantoin, and 92.1% water) | 2.2 |
| PEG-7 glyceryl cocoate | 0.01 |
| Fragrance | 0.4 |
| Citric acid (50% solution) | 0.03 |
| Glycerin | 2 |
| Sodium ascorbate | 0.25 |
| Benzophenone-4 | 0.05 |
| Litmus | 0.5 |

Example 2

The composition in Example 1 was used for comparative testing for a composition with no antioxidants, sodium ascorbate only, benzophenone only, and a combination of sodium ascorbate and benzophenone-4. The amount of water was adjusted to make a 100% composition. The compositions were aged 13 weeks at 49° C. Initially, at 4 weeks, at 8 weeks, and at 13 weeks, the compositions were measured for stability using the UV-Vis method described above, and were measured at 590 nm. The results are provided in the table below. % Change is calculated as (Initial Value−13 Week Value)/(Initial Value).

| Litmus at 0.5% concentration over 13 weeks aging at 49° C. Absorbance Values at 590 nm | | | | | |
|---|---|---|---|---|---|
| | Initial | 4 weeks | 8 weeks | 13 weeks | % Change |
| No antioxidants | 2.345 | 2.179 | 1.755 | 1.818 | 22.5% |
| Na Ascorbate (0.25%) | 2.273 | 1.981 | 1.525 | 1.527 | 32.8% |
| Benzophenone-4 (0.05%) | 2.317 | 2.009 | 1.7 | 1.543 | 33.4% |

| | Initial | 4 weeks | 8 weeks | 13 weeks | % Change |
|---|---|---|---|---|---|
| Na Ascorbate (0.25%) and Benzophenone-4 (0.05%) | 2.478 | 2.385 | 2.045 | 2.17 | 12.4% |

Litmus at 0.5% concentration over 13 weeks aging at 49° C. Absorbance Values at 590 nm As can be seen, sodium ascorbate alone and benzophenone-4 alone at their given levels do not provide the level of stability that is achieved by the combination of both together.

What is claimed is:

1. A composition comprising:
   a. at least one indicator selected from litmus;
   b. sodium ascorbate; and
   c. benzophenone-4.
2. The composition of claim 1, wherein the composition has a second light absorption value after 13 weeks at 49° C. that is no more than 20% different from a first light absorption value that is measured initially according to a UV-Vis spectrometer test for a peak absorption for the indicator.
3. The composition of claim 1, wherein the indicator is present in an amount of 0.01 to 10% by weight.
4. The composition of claim 1, wherein the sodium ascorbate is present in an amount of 0.01 to 1% by weight.
5. The composition of claim 1, wherein the benzophenone-4 is present in an amount of 0.01 to 0.1% by weight.
6. The composition of claim 1 further comprising at least one indicator selected from carmine, carminic acid, curry powder, thymol blue, pentamethoxy red, tropaeolin O, tropaeolin OO, tropaeolin OOO, 2, 4-dinitrophenol, methyl yellow, methyl orange, bromophenol blue, tetrabromophenol blue, alizarin sodium sulfonate, alpha-naphthyl red, para-ethoxychrysoidine, bromocresol green, methyl red, bromocresol purple, chlorophenol red, bromothymol blue, para-nitrophenol, azolitmin, phenol red, neutral red, rosolic acid, cresol red, naphtholphthalein, phenolphthalein, naphtholbenzein, thymolphthalein, nile blue, alizarin yellow, salicyl yellow, diazo violet, nitramine, poirrier's blue, trinitrobenzoic acid, extracts from: beets, blackberries, blueberries, carrots, cherries, delphinium petals, geranium petals, grapes, grape seeds, horse chestnut leaves, morning glories, pansy petals, petunia petals, primrose, poppy petals, purple peonies, red radish, red cabbage, rhubarb, rose petals, strawberries, tea, turmeric, tulip petals, thyme, violet petals, and vanilla.
7. The composition of claim 1 further comprising a surfactant.
8. The composition of claim 1 comprising:
   a. 0.01 to 1% by weight litmus,
   b. 0.05 to 1% by weight sodium ascorbate, and
   c. 0.05 to 0.1% by weight benzophenone-4.
9. The composition of claim 1 comprising:
   a. about 0.5 weight % litmus,
   b. about 0.25 weight % sodium ascorbate, and
   c. about 0.05 weight % benzophenone-4.
10. The composition of claim 1 further comprising glycerin.
11. The composition of claim 1 comprising:
    a. 0.01 to 1% by weight litmus,
    b. 0.05 to 1% by weight sodium ascorbate,
    c. 0.05 to 0.1% by weight benzophenone-4;
    d. glycerin in an amount up to 5% by weight;
    e. and a surfactant.
12. A method comprising:
    a. applying the composition of claim 1 to a substrate; and
    b. leaving the composition on the substrate until a color change is observed.
13. The method of claim 12, wherein:
    a. the applying the composition is to hands;
    b. the leaving the composition on the substrate comprises rubbing the hands together until the color change is observed and rinsing the hands with water.
14. The method of claim 12, wherein the composition changes from a basic composition to an acidic composition during use.
15. The method of claim 12, wherein the color change is observed before about 30 seconds.
16. The method of claim 12, wherein the color change is observed at a time of 10 to 30 seconds.

* * * * *